United States Patent
Johnston et al.

(10) Patent No.: US 8,062,839 B2
(45) Date of Patent: Nov. 22, 2011

(54) PARKIN SUBSTRATE AND ASSAY

(75) Inventors: Jennifer A. Johnston, Mill Valley, CA (US); Colleen Tsui Cutcliffe, San Francisco, CA (US)

(73) Assignee: Elan Pharma International Limited, Athlone, County Westmeath (IE)

( * ) Notice: Subject to any disclaimer, the term of this patent is extended or adjusted under 35 U.S.C. 154(b) by 252 days.

(21) Appl. No.: 12/124,984

(22) Filed: May 21, 2008

(65) Prior Publication Data

US 2009/0023178 A1    Jan. 22, 2009

Related U.S. Application Data

(60) Provisional application No. 60/939,335, filed on May 21, 2007.

(51) Int. Cl.
*C12Q 1/00* (2006.01)
(52) U.S. Cl. .......................................................... 435/4
(58) Field of Classification Search .................... 435/4
See application file for complete search history.

(56) References Cited

U.S. PATENT DOCUMENTS

2004/0214763 A1   10/2004   Corti et al.
2008/0293089 A1   11/2008   Johnston et al.

FOREIGN PATENT DOCUMENTS

EP      1 416 272 A1    5/2004
WO   WO 2008/144736 A1  11/2008

OTHER PUBLICATIONS

Choi et al. "SEPT5_v2 is a parkin-binding protein", Molecular Brain Research, 2003, 117:179-189.*

Hampe et al. "Biochemical analysis of Parkinson's disease-causing variants of Parkin, an E3 ubiquitin-protein ligase with monoubiquitylation capacity", Human Molecular Genetics, 2006, 15(13):2059-2075.*
U.S. Appl. No. 60/939,335, filed May 21, 2007, Johnston.
Hershko et al., "The Ubiquitin System," *Annual Review of Biochemistry*, 67:425-479 (1998).
Hicke, "Getting' Down With Ubiquitin: Turning of Cell-Surface Receptors, Transporters and Channels," Trends in Cell Biology, 9:107-112 (1999).
Ihara et al., "Association of the Cytoskeletal GTP-binding Protein Sept4/H5 with Cytoplasmic Inclusions Found in Parkinson's Disease and other Synucleinopathies," *Journal of Biological Chemistry*, 278(26):24095-24102 (2003).
Ihara et al., "Sept4, a Component of Presynaptic Scaffold and Lewy Bodies, is Required for the Suppression of Alpha-Synuclein Neurotoxicity," *Neuron*, 53(4):519-533 (2007).
Imai et al., "An Unfolded Putative Transmembrane Polypeptide, which can Lead to Endoplasmic Reticulum Stress, is a Substrate of Parkin," *Cell*, 105(7):891-902 (2001).
Larisch et al., "A Novel Mitochondrial Septin-Like Protein, ARTS, Mediates Apoptosis Dependent on its P-loop Motif," *Nature Biology*, 2:915-921 (2000).
PCT Search Report of Jun. 23, 2008 for application PCT/US2008/064372.
Periquet et al., "Proteomic Analysis of Parkin Knockout Mice: Alterations in Energy Metabolism, Protein Handling and Synaptic Function," *Journal of Neurochemistry*, 95(5):1259-1276 (2005).
Sawkar et al., "Chemical chaperones and Permissive Temperatures Alter the Cellular Localization of Gaucher Disease Associated Glucocerebrosidase Variants," *ACS Chemical Biology*, 1(4):235-251 (2006).

* cited by examiner

*Primary Examiner* — Sue Liu
*Assistant Examiner* — Bin Shen
(74) *Attorney, Agent, or Firm* — Alston & Bird LLP

(57) ABSTRACT

The invention provides in vitro, ex vivo, and in vivo assays for Parkin activity, in which Parkin-mediated ubiquitination of a Sept4 protein is measured. The assays may be used to screen for agents that modulate Parkin protein ligase activity.

10 Claims, 2 Drawing Sheets

PARKIN SUBSTRATE AND ASSAY

CROSS-REFERENCE TO RELATED APPLICATIONS

This application claims benefit of U.S. provisional application 60/939,335 filed May 21, 2007, the entire contents of which are incorporated herein by reference.

BACKGROUND OF THE INVENTION

Parkinson's disease (PD) is a neurological disorder characterized neuropathologically as a loss of dopamine neurons of the substantia nigra. This neuronal loss manifests clinically as alterations in movement, such as Bradykinesia, rigidity and/or tremor (Gelb et al., *Arch. Neurol.*, 56:33-39, (1999)). Human genetic data have identified genes linked to the development of PD. One of these genes was localized to chromosome 6 using a cohort of juvenile onset patients and identified as Parkin protein (Kitada et al., *Nature*, 392:605-608 (1998)). Parkin protein is an E3 ligase protein that functions in the ubiquitin-proteasome pathway (UPS) (Shimura, *Nature Genetics*, 25:302-305 (2000)). The UPS is a major cellular pathway involved in the targeted removal of proteins for degradation and E3 ligases function to identify and label substrates for degradation by cellular proteasomes (Hereshko et al., *Ann. Rev. Biochem.*, 67:425-479 (1998)) or lysosomes (Hicke, *Trends in Cell Biology*, 9:107-112 (1999)).

Another hallmark of PD is the presence of insoluble proteinaceusus cellular inclusions known as Lewy Bodies. Lewy Bodies are comprised of many proteins, the most prominent being the α-synuclein protein (Spillantini et al., *Nature*, 388: 839-40 (1997)). Point mutations in the α-synuclein gene or multiplications of the gene, result in PD (Polymeropoulos et al., *Science*, 276:2045-7 (1997); Kruger et al., *Nature Genetics*, 18:106-8 (1998)).

New therapeutic agents for treating Parkinson's disease are urgently needed. The present invention provides new methods and materials useful for identifying and validating such new therapeutic agents and for other uses.

BRIEF SUMMARY OF THE INVENTION

The present invention provides a method for detecting Parkin activity including combining a Parkin protein and a Septin-4 (Sept4) protein under conditions in which the Sept4 protein can be ubiquitinated by the Parkin ligase activity, and measuring the presence, rate or extent of ubiquitination of the Sept4 protein. In some embodiments, the Parkin protein and the Septin-4 protein are combined in vitro. In some embodiments, the Parkin protein and the Septin-4 protein are combined in a buffered reaction medium containing E1, E2, Mg-ATP, and ubiquitin. In some embodiment of the assay, Parkin activity is detected in a cell. In some embodiment of the assay, Parkin activity is detected in a cell ex vivo. In some aspects of the assay, the cell expresses endogenous Sept4. In some aspects, the cell is a primary (untransformed) cell. In some aspects, the cell used in the assay is a SHSY-5Y cell (ATCC-2266) or human fetal brain cell.

The present invention provides an assay for modulators of Parkin activity. The assay includes: (1) incubating Parkin protein and Septin-4 protein together in vitro under conditions in which the Septin-4 protein can be ubiquitinated; (2) incubating Parkin protein and Septin-4 protein in the presence of a test agent together under the conditions of (1); (3) comparing the rate or extent of Septin-4 ubiquitination in the presence of the test agent with the rate or extent of Sept4 ubiquitination in the absence of the test agent, where a relative increase in Septin-4 ubiquitination in the presence of the test agent indicates that the test agent enhances Parkin ubiquitination activity and a relative decrease in Sept4 ubiquitination in the presence of the test agent indicates that the test agent inhibits Parkin ubiquitination activity. In some embodiments of the assay, the Parkin protein and Septin-4 protein are combined in a composition containing an E1 protein, an E2 protein, ubiquitin and ATP. In some embodiments of the assay, the E2 protein is selected from the group consisting of UbcH5, UbcH7, UbcH13 and UbcH13/Uev1.

The present invention additionally provides a cell-based method for measuring Parkin activity including: (a) providing a mammalian cell expressing Parkin and expressing Sept4 and (b) measuring the rate or extent of Sept4 ubiquitination in the cell. In some aspects of the method, the Sept4 protein is expressed endogenously in the cell. In some other aspects of the assay, the Sept4 protein is expressed recombinantly in the cell. In some aspects of the method the Parkin protein is a variant or fragment of the Parkin protein. In some aspects, the Parkin protein is a variant having asparagine instead of serine at position 167; tyrosine instead of cysteine at position 212; methionine instead of threonine at position 240; tryptophan instead of arginine at position 275; glycine instead of cysteine at position 289; or leucine instead of proline at position 437.

In some embodiment, the present invention provides an ex vivo cell-based assay for modulators of Parkin activity, said assay including (a) providing a mammalian cell expressing Parkin and expressing Sept4, (b) exposing the cell to a test agent and (c) comparing the rate or extent of Sept4 ubiquitination in the presence of the test agent with the rate or extent of Sept4 ubiquitination in a control cell not exposed to the test agent, where a relative increase in Sept4 ubiquitination in the presence of the test agent indicates that the test agent enhances Parkin ubiquitination activity and a relative decrease in Sept4 ubiquitination in the presence of the test agent indicates that the test agent inhibits Parkin ubiquitination activity. In some embodiments, the Sept4 protein is expressed endogenously in the cell. In some embodiments, the Sept4 protein is expressed recombinantly in the cell. In some embodiments, the Parkin protein is a variant or fragment. In some embodiments, the Parkin protein is a variant having asparagine instead of serine at position 167; tyrosine instead of cysteine at position 212; methionine instead of threonine at position 240; tryptophan instead of arginine at position 275; glycine instead of cysteine at position 289; or leucine instead of proline at position 437.

The present invention provides a method for identifying modulators of Parkin activity, said method including: (a) providing a non-human animal co-expressing Parkin and expressing Sept4 in neuronal cells; (b) administering a test agent to the animal; (c) comparing the rate or extent of Sept4 ubiquitination in said neuronal cells of the animal in to which the test agent was administered with the rate or extent of Sept4 ubiquitination in a control animal not administered the agent, wherein a relative increase in Sept4 ubiquitination in the presence of the therapeutic agent indicates that the therapeutic agent enhances Parkin ubiquitination activity and a relative decrease in Sept4 ubiquitination in the presence of the therapeutic agent indicates that the therapeutic agent inhibits Parkin ubiquitination activity. In one embodiment the animal is a rodent (e.g., mouse) or non-human primate. In one embodiment the animal expresses a transgene or transgenes in said cells, said transgene(s) encoding either or both of Septin-4 and Parkin.

BRIEF DESCRIPTION OF THE DRAWINGS

FIG. 2A shows staining with anti-Sept4 antibodies and FIG. 2B shows staining with anti-Parkin.

FIG. 2C is a Western blot showing that Sept4 ubiquitination is not specific for a particular Parkin-E2 combination. An in vitro ubiquitination assay using various E2 enzymes was utilized to assess ubiquitination Sept4. Samples were incubated for 0, 30, or 60 minutes at 37° C., and immunoblotted using antibody to Sept4. The asterisk indicates a cross-reacting band.

FIG. 2D is a Western blot showing that Sept4 ubiquitination is specific to the E3 ligase, Parkin. An in vitro ubiquitination assay using various E3 ubiquitin ligases to assess ubiquitination of Sept4. Samples were incubated for 0 or 30 minutes at 37° C., and immunoblotted using antibody to Sept4.

DETAILED DESCRIPTION OF THE INVENTION

I. Introduction

Figure 1:
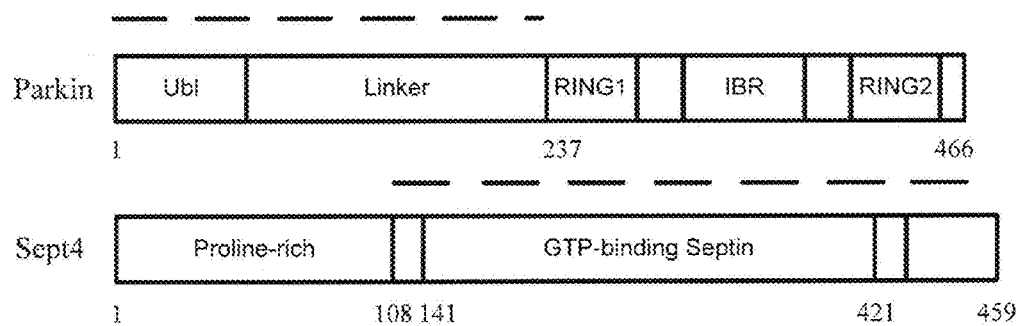
FIG. 1A shows Parkin and Sept4 protein domains. Parkin was used as bait in a yeast-2-hybrid screen either as full-length protein or using amino acids 1-237 of Parkin. The most frequent hit, Sept4, was identified a total of 82 times from both screens, spanning the entire sequence of Sept4, except the first 117 amino acids. Dashed line indicates interaction domains of Parkin and Sept4.
FIG. 1B is a Western blot illustrating the interaction of Parkin and Sept4 in HEK293 cells. Stable HEK293 cell lines overexpressing Parkin were transfected with either pcDNA (C) or Sept4 cDNA (S4). Parkin was immunoprecipitated from cell lysates and bound material was analyzed by immunoblotting with antibody to Sept4. Cellular extract (CE) is shown for reference.
FIG. 1C is a Western blot showing that Parkin and Sept4 interact in human cortical cells. Lysates prepared from either human cortical neurons (HCC) transfected with empty lentivirus or HCC transfected with Parkin lentivirus were incubated with antibody to Parkin and protein G beads for 3 hours. Beads were washed (W) and unbound (FT) and bound proteins (E) were analyzed by immunoblotting.
FIG. 1D is a Western blot showing that Sept4 is ubiquitinylated (as evidenced by higher molecular weight bands) in 26S proteosome-inhibited cells. HEK293 cells and parkin overexpressing HEK293 cells were transfected with either pcDNA or with pSept4, treated with DMSO or epoxomicin and cell lysates were immunoblotted with antibody to Sept4.
Figure 1:
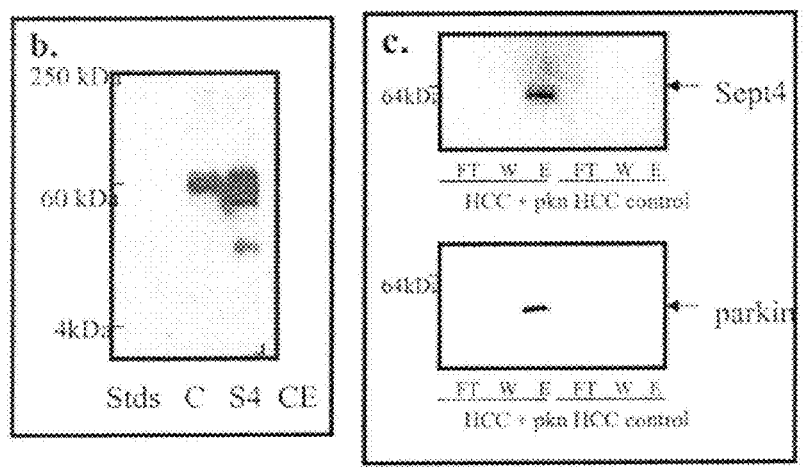
Figure 1:
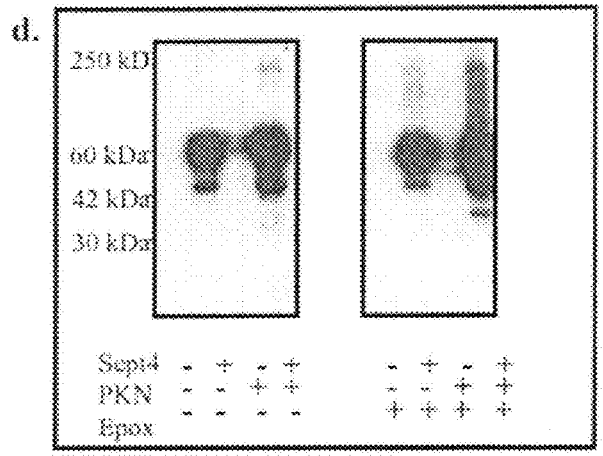

Genetic data have established that loss of Parkin protein activity in humans results in the progressive loss of dopaminergic neurons in the substantia nigra and eventually to Parkinson's Disease (PD). Parkin protein is an E3 (ubiquitin) ligase protein that operates in conjunction with an E1 ubiquitin-activating enzyme and an E2 ubiquitin-conjugating enzyme. The E1 enzyme uses ATP to activate ubiquitin for conjugation and transfers it to an E2 enzyme. Parkin interacts with the E2 and transfers the ubiquitin to a lysine E-amino group on a protein substrate. The consecutive addition of ubiquitin moieties to a substrate generates a polyubiquitin chain. Parkin activity can be assayed by measuring the rate or extent of transfer of ubiquitin to the substrate or "target protein".

Known Parkin substrates include alpha-synuclein and the Parkin protein itself (autoubiquitination). It has now been discovered Septin 4 (Sept4) is also a substrate for the Parkin ligase. This discovery has particular significance because the inventors have shown the Sept4 protein is not a promiscuous ubiquitination substrate but is specifically ubiquitinated by Parkin. Thus the ubiquitination of Sept4 can be used as a direct measure of Parkin ligase activity. For example, Parkin activity can be assayed by measuring the rate or extent of ubiquitination of Sept4 in vitro, ex vivo or in vivo.

Assays for Parkin ligase activity are useful in a variety of applications and are particularly valuable for screening and evaluating drug candidates for use in treating PD and other neurological diseases. Assays are also useful for detecting the presence or activity of Parkin in a biological sample, evaluating the integrity of recombinant or purified Parkin protein, evaluating the ligase activity of modified or variant Parkin proteins, and other uses that will be apparent in view of this disclosure.

II. In Vitro Assays of Parkin Ligase Activity

In one aspect, the invention provides an in vitro method for measuring Parkin activity by (1) incubating Parkin protein and Sept4 protein together under conditions in which the Sept4 protein can be ubiquitinated, and (2) measuring the rate or extent of ubiquitination of the Sept4 protein.

A number of assays for detecting ubiquitination by Parkin and other E3 ligases are well known in the art and can be used in the present invention. Buffers, reagents and assay conditions in which Parkin ligase activity is retained may be used in the Parkin activity assays of the current invention, using a Sept4 protein as a substrate. Thus, one of ordinary skill in the art, guided by this disclosure (including the identification of Sept4 protein as a Parkin substrate) will be able to adapt such assays for measuring Sept4 ubiquitination by Parkin. For example, Parkin and Sept4 may be combined and incubated in the presence of E1 (e.g., UBA1 Genbank accession No. X55386), E2 (e.g., UbcH7), Mg-ATP, ubiquitin, and an aqueous buffer (e.g., 50 mM HEPES/50 mM NaCl pH 8.8), and the rate or extent of conjugation of ubiquitin to Sept4 protein can be measured. As used herein "incubate" has its normal meaning of combining components and allowing an enzymatic reaction(s) to proceed, usually at room temperature or physiological temperature. Exemplary assay conditions are described herein, for illustration and not for limitation.

The rate or extent of ubiquitination of a Sept4 protein can be measured in a variety of ways, and the present invention is not limited to a particular method. One way to measure Sept4 ubiquitination involves carrying out a ubiquitination reaction, separating proteins in the reaction mixture by electrophoresis, transferring the separated proteins to a substrate (Western Blotting), probing the Western Blot with an anti-Sept4 antibody, and detecting changes in Sept4 mobility that reflect attachment of ubiquitin to the Sept4 substrate (see Examples). Other methods of measuring ubiquitination can be used, including without limitation immunologically based assays (ELISA, immunoprecipitation, see Harlow and Lane, *Antibodies, A Laboratory Manual*, Cold Spring Harbor Publications, New York, 1988, incorporated by reference herein), mass spectroscopic methods, electromagnetic spectrum spectroscopic methods, chromatographic methods, ubiquitination using detectably labeled ubiquitin, and other approaches that will be apparent to those of skill in the art. For example, in a plate assay, fluorescein-tagged ubiquitin, can be detected directly using a fluorescence plate reader, biotin-tagged ubiquitin can be detected using labeled strepavidin (e.g., strepavidin-HRP or 1:5000 Neutravidin-HRP [Pierce Chemical Comp. Rockford, Ill.]), and epitope-tagged ubiquitin can be detected in an immunoassay using anti-tag antibodies. Methods for detection of ubiquitinated Sept4 will depend on the label or tag used.

A large number of in vitro assay formats can be used in the practice of the invention. For example, the assay components can be in solution, or one or more may be immobilized. A ubiquitination assay may be carried out, for example, by adding a ubiquitination reaction mixture including Parkin and other reagents to a well, tube or chamber and the ubiquitination reaction occurs. The level of resulting ubiquitinated Sept4 protein ("uSept4") is measured using immunological methods (e.g., binding a detectably labeled anti-ubiquitin or anti-Sept4 antibody to the complex), other binding methods (e.g., using biotinylated ubiquitin in the reaction and detecting the uSept4 using an avidin-linked probe) or by using a detectably labeled ubiquitin in the assay.

In one approach, Sept4 is immobilized. For illustration, in one assay a Sept4 protein is immobilized on a surface (such as a microwell plate, Sepharose beads, magnetic beads, and the like) and incubated with a ligase reaction mix that includes Parkin, E1, E2, ubiquitin, and ATP. In one embodiment, a Sept4 protein is immobilized in wells of a 96-well or 386-plate (available from e.g., Immulon [Waltham, Mass.]; Maxisorb [Life Technologies, Karsruhe, Germany], or the like). Any method for immobilizing a Sept4 protein that does not interfere with ubiquitination can be used. For example, in one approach epitope-tagged Sept4 protein is immobilized via the tag to a substrate. In another approach, Sept4 may be immobilized using an antibody binding system in which an antibody that recognizes a Sept4 epitope is used. Alternatively the antibody can recognize an epitope tag fused to the Sept4 protein. In some approaches immobilization involves interactions other than antibody-mediated interactions. For example, in one approach, a Sept4 protein with a N-terminal 6× His tag is immobilized using a nickel-coated assay plate. In one approach, a biotinylated component is immobilized via an interaction with avidin.

After a blocking step, a ligase reaction mix including E1 (ubiquitin-activating enzyme), E2 (ubiquitin conjugating enzyme), ATP-Mg, ubiquitin (usually labeled ubiquitin) and Parkin (Parkin E3 ligase) is combined with an immobilized Sept4 protein. Optionally E1 is epitope tagged (e.g., with GST or $His_6$). The reaction components can be added in any desired order. ATP can be added last, if desired, to initiate the reaction. Those of skill in the art will appreciate that modification to the reaction mix can be made without affecting the functional effect of the assay. For instance, Tris, Bicine and other buffers can be used instead of HEPES.

An exemplary reaction mix is:
Parkin protein (e.g., 2-10 µg)
500 nM 1:1 Biotin:ubiquitin (biotinylated ubiquitin)
2-6 nM GST-E1
300 nM E2 (UbcH7)
10 mM MgATP
50 mM HEPES/50 mM NaCl pH 8.8

A reaction component, typically ATP, can be omitted from certain samples as a negative control. In one embodiment, the assay is carried out in a 96 or 384 well plate format. The plate is incubated for a period of time (e.g., such as 60 minutes at room temperature or 10-90 minutes at 37° C.). Plates are washed to remove soluble reagents and the presence or amount of ubiquitin (i.e. the ubiquitin component of ubiquitinated Sept4) is determined. The wash solution may be, for example, 50 mM HEPES/50 mM NaCl.

Prior to addition of reaction components, the surface may be treated with a blocking solution to reduce nonspecific binding of proteins, especially E1, to the plate. Blocking agents include SuperBlock (Pierce Chemical Company, Rockford, Ill.); SynBlock (Serotec, Raleigh, N.C.); SeaBlock (CalBiochem, Darmstadt, Germany); metal chelate block (Pierce Chemical Company, Rockford, Ill.); 1% casein; glutathione; and various combinations of these. After the blocking step, the wells can be washed with SuperBlock wash (Pierce Chemical Company, Rockford, Ill.) or Ligase Buffer Wash (50 mM HEPES/50 mM NaCl). In one embodiment, Immulon 96 or 384 well plates are blocked with 1% casein in 50 mM HEPES/50 mM NaCl and washed using 50 mM HEPES/50 mM NaCl/4 mM DTT.

In another approach, the ubiquitination assay can be carried out in solution (i.e., without immobilizing Sept4 protein or other component, and the reaction solution (or an aliquot thereof) is then transferred to a capture plate. In an exemplary reaction, the reaction components are assembled in 50 microliter volume and the assay is run for 10-90 minutes (e.g., 60 minutes) at 37° C. At the end of the assay and/or at various time points in the assay, the reaction mix, or an aliquot thereof, is transferred to a capture plate (e.g., 96 or 384 well plate) containing an immobilized moiety that binds Sept4 (e.g., anti-Sept4 antibody or nickel for His-tagged Sept4) or binds ubiquitin (e.g., anti-ubiquitin antibody, nickel for His-tagged ubiquitin, or contains an anti-epitope tag antibody (such as anti-FLAG, GST, $His_6$, Myc, MBP, etc.) for epitope-tagged ubiquitin.

Assays can be designed to measure total ubiquitination per unit mass of Sept4 at a particular end point ("extent" of ubiquitination) and/or to measure the extent of poly-ubiquitination of Sept4 molecules (i.e., the length of ubiquitin chains). Assays can be designed to measure ubiquitination at multiple time points (e.g., see Example 2) to determine the level of ubiquitination per unit time ("rate" of ubiquitination) or under varying conditions.

As noted above, in general, in vitro assays of the invention are conducted under conditions in which Parkin-based ubiquitination of Sept4 (e.g., Sept4var3) occurs. For example, the reaction generally includes Parkin protein, a Sept4 protein, an E1 (e.g., UBA1, UBA2), an E2 (e.g., UbcH2, UbcH5, UbcH6, UbcH7, UbcH8, UbcH13), Mg-ATP, and ubiquitin in a buffered solution (e.g., HEPES, TRIS or BICINE buffers at physiological pH and osmolarity). Assay components may be made using methods known in the art or as described below, or may be purchased. For example, purified ubiquitin pathway enzymes can be obtained from Boston Biochem Inc. (840 Memorial Drive, Cambridge, Mass. 02139). Also see Wee et al., *J. Protein Chemistry*, 19:489-98 (2000). Parkin, Sept4, E1, E2, and ubiquitin may be purified and/or recombinant and may be mammalian (e.g., human, rabbit, or mouse) or from other eukaryotes. As discussed herein, a variety of Parkin variants may be used. In some versions of the assay, the reaction components are derived from the same species (e.g., human Parkin, Sept4, E1, E2 and ubiquitin or mouse Parkin, Sept4, E1, E2, and ubiquitin). For illustration and not limitation, particular assay components are further discussed below.

Although a selection of assay approaches have been described above, it will be appreciated that there are numerous possible approaches to making and detecting ubiquitinated Sept4 (uSept4) and it will be well within the ability of a one of skill to identify many variations of the above-described assays.

a) Parkin

Mammalian Parkin proteins are used in this assay. The Parkin protein used in the assay can be a purified or recombinant protein preparation. Alternatively, Parkin ligase activity in a patient sample (e.g., biopsy) or other source believed to contain Parkin can be measured. In one preferred embodiment the Parkin is mouse or human. The amino acid sequences of Parkins (e.g., human and mouse Parkin) are known. An exemplary sequence for a human Parkin protein is found, for example, under NCBI accession number BAA25751. An exemplary sequence for a mouse Parkin protein is found, for example, under NCBI accession number AAI13205. Parkin used in assays of the invention can have a wild-type sequence. Alternatively, the Parkin may be allelic variant, another naturally occurring variant, or a recombinantly produced variant. Parkin used in the assays can be a variant that deviates from the wild-type sequence by a substitution, insertion or deletion of one or more residues so long as the variant retains at least some ligase activity. In some versions, Parkin variants that have an activity level different from wild-type are used (e.g., variants having asparagine instead of serine at position 167; tyrosine instead of cysteine at position 212; methionine instead of threonine at position 240; tryptophan instead of arginine at position 275; glycine instead of cysteine at position 289; or leucine instead of proline at position 437). Optionally a variant that confers a different phenotype than wild-type Parkin when expressed in a cell or organism is used. A parkin form suitable in the present assay will generally retain at least 50% of the ligase activity of the same molar amount of the wild-type human parkin, preferably at least 75%, often at least 80%, and most very at least 90%. In addition, Parkin fragments can be used, provided they retain least some ligase activity. Often such fragments are at least 100, at least 200, at least 300 or at least 400 amino acids in length and may comprise at least 200, at least 300, or at least 400 residues of a naturally occurring Parkin protein. In some embodiments variants of Parkin used in the present invention share at least 80% sequence identity, at least 90% sequence identity, and sometimes at least 95% sequence identity, with a naturally occurring form of Parkin. Sequence identity between two proteins may be determined by optimally aligning the two protein sequences. Proteins can be aligned manually or using computer-implemented algorithms such as ClustalW and the NCBI (National Center for Biotechnology Information, ncbi.nlm.nih.gov/) alignment programs, using default parameters. Examples of algorithms that are suitable for determining percent sequence identity and sequence similarity are the BLAST and BLAST 2.0 algorithms, which are described in Altschul et al. (1990) *J. Mol. Biol.* 215: 403-410 and Altschul et al. (1977) *Nucleic Acids Res.* 25: 3389-3402, respectively. The algorithm involves first identifying high scoring sequence pairs (HSPS) by identifying short words of length W in the query sequence, which either match or satisfy some positive-valued threshold score T when aligned with a word of the same length in a database sequence. The BLAST algorithm parameters W, T, and X determine the sensitivity and speed of the alignment. For amino acid sequences, the BLASTP program uses as defaults a word size (W) of 3, an expectation (E) of 10, and the BLOSUM62 scoring matrix (see Henikoff & Henikoff, *Proc. Natl. Acad. Sci. USA* 89:10915 (1989)).

Methods for recombinant expression of Parkin, are well known in the art. See, for illustration and not limitation, Marr et al., 2003, *J. Neurosci.,* 23:1992-6. Parkin may be expressed as a fusion protein and may include, for example, an epitope tag to facilitate purification and/or binding to a substrate such as a microtiter well. Parkin may be recombinantly expressed in *E. coli* or other bacteria and purified as described in copending application Ser. No. 11/638,242 for "Assay for Parkinson's Disease Therapeutics and Enzymatically Active Parkin Preparations," incorporated herein by reference. This purification method includes a dialysis step in which protein is refolded in an arginine-containing solution. Methods for purification of Parkin protein from cells are also known.

b) Septin 4

Three splice variants of Septin 4 have been identified to date: Sept4var1 (NCBI accession number NP_004565), Sept4var2 (also known as "ARTS") (NP_536340) and Sept4var3 (NP_536341). Sept4var1 and Sept4var3 have the same sequence except Sept4var1 contains an additional 21 amino acids at the N-terminus. Sept4var2 (ARTS) shares sequence identity with variants 1 and 3 for residues 1-247 and then diverges in sequence for amino acids 247-274 (see Larisch et al., 2000, *Nature Cell Biol* 2:915-20 incorporated by reference herein). Also see Chance et al., 2006, "Inherited focal, episodic neuropathies: hereditary neuropathy with liability to pressure palsies and hereditary neuralgic amyotrophy" *Neuromolecular Med.* 8(1-2):159-74; Spiliotis et al., 2006 "Here come the septins: novel polymers that coordinate intracellular functions and organization" *J Cell Sci.* 119(Pt 1):4-10; Hall et al., 2004, "The pathobiology of the septin gene family" *J Pathol.* 204(4):489-505; each incorporated by reference herein.

As demonstrated in the Examples below, Sept4var3 is a Parkin substrate. In assays of the invention, the Sept4 protein may be Sept4var3. Alternatively the Sept4 protein may be Sept4var1. Alternatively the Sept4 protein may be Sept4var2. Variants, fragments and mixtures of isoforms may also be used. Isoform 1 and isoform 3 of Sept4 differ only at 21 amino acid residues at the amino terminus and are believed to have equivalent interactions with Parkin. Sept4var2 (ARTS) has homology at the amino terminal 1-247 residues. Co-immunoprecipitiation experiments from neuronal cells demonstrated that Sept4var2 and Parkin interact with each other. By analogy to Sept4var3, it is believed that Sept4var2 is ubiquitinated by Parkin. Ubiquitination of Sept4var2 by Parkin can easily be detected using the in vitro assay described herein, or by measuring Sept4var2 ubiquitination in vivo or ex vivo.

Sept4 variants that deviate from the sequence of naturally occurring isoforms can be alternatively used so long as they retain their ability to serve as a ubiquitination substrate for Parkin. Whether a particular Sept4 variant can act as a ubiquitination substrate for Parkin can be tested using the methods described in this invention, for instance, ubiquitination of a Sept4 variant by Parkin can be assessed as described in Example 5.

In some embodiments, truncated forms of Sept4 can be used with the methods of the present invention. For example, as demonstrated in the experimental examples below, Sept4 variants missing 117 amino acids from the N-terminus retain their ability to be ubiquitinated by Parkin and can, thus, be used in assays of the invention. Truncated variants may be, in some embodiments, at least 100, at least 150, at least 157, or at least 200 amino acids in length. In some embodiments, other variants of Sept4 can be used to practice the methods of this invention, e.g., Sept4 variants that differ from Sept4var1, Sept4var2 or Sept4var3 by insertions, deletions or substitutions. Useful variants retain the property of being a Parkin ubiquitination substrate, which can be tested using routine assays such as the formats described herein. Other variants of Sept4 that can be used in the present invention include variants that share at least 80% sequence identity, at least 90% sequence identity, or at least 95% sequence identity, with a Sept4 protein. Those of skill in the art can easily determine sequence identity shared between a variant and the parental protein by optimally aligning the two protein sequences. Alignment programs such as ClustalW and the NCBI alignment programs described above are exemplary programs that can be used for optimally aligning two proteins.

A Sept4 protein may be expressed as a fusion protein and may include, for example, an epitope tag to facilitate purification and/or binding to a substrate such as a microtiter well. Other methods of protein expression in bacterial, insect and mammalian systems are known to those of skill in the art and can be applied to express and purify Sept4. For example, Ihara and colleagues use a baculoviral system to express histidine tagged Sept4 proteins cloned from human and mouse (Ihara et al., 2007, *Neuron,* 53:519-33).

c) Ubiquitin, Ubiquitin-Activating Enzyme (E1) & Ubiquitin-Carrier Protein (E2)

Ubiquitin, ubiquitin-activating enzyme (E1) and ubiquitin-carrier protein (E2) may be produced using routine recombinant methods or may be purchased from commercial vendors such as Boston Biochem (Cambridge, Mass.). Examples of E2 that can be used in the ubiquitination reactions of the present invention include, but are not limited to UbcH2, UbcH5, UbcH7, UbcH8, UbcH10 and UbcH13. Ubiquitin-Activating Enzyme (E1) and Ubiquitin-Carrier Protein (E2) may be human, from a non-human mammal, or from a different eukaryote (e.g., *S. cerevisiae*).

Ubiquitin is commercially available from, e.g., Boston Biochem Inc. (840 Memorial Drive, Cambridge, Mass. 02139). Biotinylated ubiquitin can be purchased or can be prepared using art known means. One biotinylated ubiquitin preparation is prepared by resuspending 50 ug of biotin-ubiquitin (UB-560, Boston Biochem) in 29.2 ul of a 1 mM methylated ubiquitin (U-502, Boston Biochem) solution, resulting in 30 ul of about 1.17 mM ubiquitin with approximately 17% biotinylated. When ubiquitin is tagged (e.g., with an epitope tag) the tag is usually fused to the N-terminus of ubiquitin or otherwise attached in a way the does not interfere with ubiquitination.

d) Antibodies

Antibodies may be used in the assays of the invention for detection, immobilization and other purposes. Antibodies to Parkin, Sept4 and ubiquitin are commercially available (e.g., the 1A1 anti-Parkin antibody is available through IBL, Minneapolis, Minn.; the anti-Sept4 SC-20179 antibody is available from Santa Cruz Biotechnology, Santa Cruz, Calif.) or can be made using routine methods. In some versions of the assay, eptiope tagged proteins are recognized using an antibody that recognizes the tag.

III In Vitro Screening for Modulators of Parkin Ligase Activity

As noted above, the assays of the invention find application in screening for modulators of Parkin protein activity. For example, agents, such as chemical chaperones that stabilize Parkin (e.g., Parkin variants) are potential agents for treatment of Parkinson's Disease. In one embodiment, an in vitro assay is used to determine whether a candidate agent is useful for treating Parkinson's disease. The assay can involve measuring the Sept4 ubiquitination activity of a purified (or partially purified) Parkin protein in the presence of the compound and comparing the ubiquitination activity of the Parkin protein in the presence of the compound with ubiquitination activity of purified Parkin protein in the absence of the compound. The ability of an agent to increase ubiquitination of Sept4 protein is indicative of an agent useful for treating Parkinson's disease and a candidate for further testing.

Thus, in one aspect the invention provides an assay for modulators of Parkin activity. The assay may involve (1) incubating Parkin protein and Sept4 protein together under conditions in which the Sept4 protein can be ubiquitinated; (2) incubating Parkin protein, a Sept4 protein, and a test agent together under the conditions of (1); and (3) comparing the rate or extent of Sept4 ubiquitination in the presence of the test agent with the rate or extent of Sept4 ubiquitination in the absence of the test agent, where a relative increase in Sept4 ubiquitination in the presence of the test agent indicates that the test agent enhances Parkin activity and a relative decrease in Sept4 ubiquitination in the presence of the test agent indicates that the test agent inhibits Parkin activity. Usually reactions with and without the test agent are run in parallel. However, it is also possible to run the control reactions at different times. For example, in one version the assay involves (1) incubating Parkin protein, Sept4 protein, and a test agent together under conditions under which Parkin protein can ubiquitinate Sept4, and (2) comparing the rate or extent of Sept4 ubiquitination in the presence of the test agent with the rate or extent of Sept4 ubiquitination in the absence of the test agent (e.g., a predetermined value), where a relative increase in Sept4 ubiquitination in the presence of the test agent indicates that the test agent enhances Parkin activity, and a relative decrease in Sept4 ubiquitination in the presence of the test agent indicates that the test agent inhibits Parkin activity. It is also possible to assay multiple agents in the same reaction, in batches or combinations. The reaction components may be combined in any order. For example, the test agent may be added prior to initiation of the ligation reaction (e.g., addition of ATP) or may be added after the ligation reaction has commenced.

There is no particular limitation on the types of agents that can be screened the ability to modulate (inhibit or increase) Parkin activity. A variety of classes of test agents can be used. For example, a number of natural and synthetic libraries of compounds can be used (see NCI Open Synthetic Compound Collection library, Bethesda, Md.; chemically synthesized libraries described in Fodor et al., *Science,* 251:767-73 (1991); Medynski, *BioTechnology,* 12:709-710 (1994); Ohlmeyer et al., *Proc. Natl. Acad. Sci. USA,* 90:10922-10926 (1993); Erb et al., *Proc. Natl. Acad. Sci. USA,* 91:11422-11426 (1994); Jayawickreme et al., *Proc. Natl. Acad. Sci. USA,* 91:1614-1618 (1994); and Salmon et al., *Proc. Natl. Acad. Sci. USA,* 90:11708-11712 (1993)). In one embodiment, the agent is a small molecule, such as a molecule with a molecular weight less than 1000, and often less than 500. Preferably the agent can cross the blood-brain barrier. In one embodiment the agent is a "chemical chaperone", capable of stabilizing Parkin (i.e., maintaining Parkin in an active conformation even when over-expressed) or induce proper folding of misfolded Parkin variants.

It will be understood that, as used herein, reference to an "agent useful for treating Parkinson's Disease" or "candidate compound for treatment of Parkinson's disease" refers to a compound identified as being more likely than other compounds to exhibit therapeutic or prophylactic benefit for patients with Parkinson's disease, i.e., a drug candidate. It will be understood by those familiar with the process of drug discovery that a drug candidate may undergo further testing (e.g., in vivo testing in animals) prior to being administered to patients. It will also be understood that the agent approved for administration to humans may be a derivative of, or a chemically modified form of, the drug candidate.

IV Cell-Based ("Ex Vivo") Assays of Parkin Ligase Activity

In one aspect the invention provides a cell-based method for measuring Parkin activity by (a) providing a mammalian cell expressing Parkin and expressing a Sept4 protein; and (b) measuring the rate or extent of Sept4 ubiquitination. The assay can be used to compare the effect of the cell environment (e.g., co-expressed proteins) on Parkin activity, to compare the activities of Parkin variants, in drug screening assays, and for other uses.

Cells expressing Parkin and Sept4 can be cells that naturally express one or both of the proteins. Any of a variety of cells can be used, including HEK293 cells (ATCC CRL-1573), SHSY-5Y cells (ATCC-2266), COS cells (CRL-1651); CHO cells (ATCC-CCL-61) or other mammalian cell lines. In one embodiment, the cell expresses endogenous Sept4 and endogenous Parkin. Cells expressing endogenous Sept4 include cell lines (e.g., neuronal cell lines such as SHSY-5Y) and primary cultures (e.g., human fetal brain cells). Primary cultures may be prepared as described in Ihara et al., 2007, *Neuron*, 53:519-33. Alternatively, either or both of the proteins can be exogenous to the cell and recombinantly expressed. Cells can be stably or transiently transfected. Preferably the cells are stable transfectants for consistency across multiple assays. In one embodiment, the cell expresses endogenous Sept4 and exogenous Parkin. In one embodiment, the cell expresses endogenous Parkin and exogenous Sept4. In one embodiment, the cell expresses endogenous Sept4 and endogenous Parkin. In one embodiment, the cell expresses exogenous Parkin and exogenous Sept4. In certain preferred embodiments the cell expresses endogenous Parkin and/or Sept4 protein, and additionally the cell expresses an exogenous (recombinant) form of Parkin and/or Sept4 protein.

When cells expressing recombinant Parkin are used, the Parkin may be expressed using an expression vector. In one embodiment the expression vector encodes a wild-type Parkin. For example, the cDNA for human Parkin (NM004562) can be inserted into the HindIII/XbaI sites of the vector pcDNA3.1 (Invitrogen, San Diego Calif.) for use in this assay. In another embodiment, an expression vector encoding a Parkin mutant is used. As described in copending application Ser. No. 11/638,242 expression of certain Parkin mutants results in inhibition of proteasome function. Exemplary Parkin mutants include S167N, C212Y, T240M, R275W, C289G, P437L. In some embodiments R275W, C212Y or C289G is used. Assays using Parkin mutants can be used as an alternative to, or in combination with, assays using wild-type Parkin. In some embodiments the Parkin and/or Sept4 proteins are variants and/or fusion proteins. Examples and properties of variants described hereinabove (as suitable for in vitro assays) can also be recombinantly expressed in a cell and ubiquitination of Sept4 measured.

When cells expressing recombinant Sept4 are used, the Sept4 may be a wild-type form (e.g., BAA25751) or variant. Examples and properties of variants suitable for in vitro assays (described above) can also be recombinantly expressed a cell and ubiquitination by Parkin measured. Variant proteins are typically introduced into the cell using an expression vector. For example, pcDNA3.1 can be used as an expression vector encoding a Sept4 variant. Alternatively a Sept4 variant can be expressed from a lentiviral expression vector.

Methods for recombinant expression are known. Expression vectors, methods for transient transfection, and methods for cell culture suitable for the practice of the invention are well known in the art and only briefly described here. As is well known, expression vectors are recombinant polynucleotide constructs that typically include a eukaryotic expression control elements operably linked to the coding sequences (e.g., of Parkin). Expression control elements can include a promoter, ribosome binding sites, RNA splice sites, polyadenylation sites, and transcriptional terminator sequences. The expression vectors are typically replicable in the host organisms either as episomes or as an integral part of the host chromosomal DNA. Examples of mammalian expression vectors include pcDNA 3.1 (Invitrogen, San Diego, Calif.); pEAK (Edge Biosystems, Mountain View, Calif.); and others (see Ausubel et al., *Current Protocols In Molecular Biology*, Greene Publishing and Wiley-Interscience, New York, as supplemented through 2005). Commonly, expression vectors contain selection markers, e.g., ampicillin-resistance or hygromycin-resistance, to permit detection of those cells transformed with the desired DNA sequences. Methods for transfection and culture of cells are also well known. See, for example, Sambrook et al. 1989, *Molecular Cloning: A Laboratory Manual*, 2nd Edition, Cold Spring Harbor Laboratory press; and in Ausubel, 1989, supra.

V. Cell-Based Screening for Modulators of Parkin Ligase Activity

The cell-based assays of the invention are useful in screening for modulators of Parkin protein activity to identify candidate compounds for treatment of Parkinson's disease. In one aspect, the effect of an agent on Parkin activity can be assessed in a cell-based assay that involves (a) providing a mammalian cell expressing Parkin and expressing Sept4; (b) exposing the cell to a test agent; (c) comparing the rate or extent of Sept4 ubiquitination in the presence of the test agent with the rate or extent of Sept4 ubiquitination in a control cell not exposed to the test agent, where a relative increase in Sept4 ubiquitination in the presence of the test agent indicates that the test agent enhances Parkin activity and a relative decrease in Sept4 ubiquitination in the presence of the test agent indicates that the test agent inhibits Parkin activity.

Cells may be exposed to the test agent by adding the agent to cell culture medium. In one approach, cells expressing the Sept4 protein are transfected with the Parkin-encoding expression construct. The cells may be cultured for 1-10 days, preferably 2 to 5 days (e.g., 3 days) and then exposed to a test agent. The duration of the exposure can vary, but will usually be from 1 to 24 hours, preferably from 4 to 16 hours. Similarly, a variety of concentrations of agent can be tested. It will be appreciated that the concentration will vary depending on the nature of the agent, but is typically in the range of 1 nM to 5 µM. Typically several different concentrations of test agent are assayed (e.g., 1 nM, 10 nM, 100 nM, 1 µM, 10 µM and 100 µM) along with a zero concentration control. Test agents (e.g., polypeptides, inhibitory nucleic acids, etc.) can also be introduced by recombinant expression in the cell. Alternatively, a test agent is added to a cell extract or homogenate.

In one embodiment of the invention, HCC cells are grown to 75% density in culture wells of a six-well cell culture plate (e.g., each well approximately 30 mm in diameter). The cells are transfected the Parkin expression vector described above, using approximately 2.5 µg of plasmid per well, and the cells cultured for about 3 days (e.g., 2 to 5 days) prior to analysis with a test agent.

VI Animal-Based ("In Vivo") Assays of Parkin Ligase Activity

Assays can also be carried out using animals. In some aspects, the present invention provides an in vivo model for assessing Parkin ligase activity in an animal naturally expressing a Parkin ligase protein and a Sept4 protein. Assays for assessing protein activity from an in vivo sample are known to those of skill in the art. The assay can be performed, for example, by making an extract of a tissue expressing Parkin and Sept4. The extract is typically made using physiologic conditions to maintain the natural ubiquitination state of the proteins in the extract. Levels or presence of ubiquitination of the Sept4 proteins in the extract are then detected. The Sept4 proteins can be isolated and detected from native tissue samples, using, for example, anti-Sept4 antibodies. Methods of detecting a ubiquitinated protein are well known to those of skill in the art. For example, Sept4 proteins can be isolated from the extract by using anti-Sept4 antibodies, and the pure or semi-pure Sept4 proteins are then typically run on an SDS-PAGE gel followed by Western blotting with anti-ubiquitin antibodies to detect the presence and level of ubiquitination of the Sept4 proteins.

In some aspects, including transgenic animals such as a mouse expressing a human Park and/or human Sept4 protein are used in the assay. In one embodiment Parkin activity is assessed in an animal engineered to express or over-express a Sept4 protein and a Parkin protein. Methods of producing transgenic animals are well known to those of skill in the art. For example, a tetracycline inducible expression mouse transgenic system is reviewed by Sun et al. 2007, *Acta Biochim Biophys Sin* (*Shanghai*), 39(4):235-46.

In some other aspects, an animal expressing Sept4, but not expressing Parkin; e.g., an animal engineered not to express Parkin, such a Parkin gene knock-out animal, is used to compare the levels of ubiquitination of the recombinantly or intrinsically expressed Sept4 protein in the presence and absence of Parkin ligase; thus providing a comparative assessment of Parkin ligase activity. In some embodiments RNA silencing technology can be used for the down-regulation of expression or inhibition of expression of Sept4 or Parkin. Use of RNAi technology in neurodegenerative disorders is described in Farah et al., 2007, *Curr Drug Deliv.*, 4:161-7 (2006). Sept4−/− knock out mice are described, e.g., in Ihara et al., 2005, *Dev Cell* 8:343-352.

In some aspects, an in vivo animal system for measuring Parkin activity based on the ubiquitination or level or ubiquitination of its Sept4 protein substrate can be used in assessing the activity of a treatment agent or potential drug on Parkin activity. In such an aspect of this invention, the animal systems described above can be used to detect the ubiquitination or level of ubiquitination of Sept4 in the presence and absence of drugs or other treatment agents. Test agents can be administered to test animals by feeding the agent to the animal, or by injection, infusion or other know methods for drug administration.

VII. EXAMPLES

Example 1

Methods and Materials

Plasmids and cell lines and antibodies: HEK293 cells were obtained from ATCC and grown in DMEM/10% FBS. HCC were prepared as described (Malinin et al., 2005, PNAS 102 (8):3058-63). Parkin cDNA (NM_004562) was cloned into the pGEX6P-1 vector for bacterial expression, the pCDNA3.1 vector for expression in mammalian cells, and the Lentiviral expression using methods and vectors as described (Marr et al., *J. Neurosci.* 23(6):1992-6 (2003)). Sept4Var3 cDNA (NM_080416.1) was obtained from Origene, Inc (Rockville, Md.) and the open reading frame was cloned into pGEX6P-1 for bacterial expression and pcDNA3.1 for mammalian expression. The commercial sources for the Parkin antibody 1A1 (IBL, Minneapolis, Minn.) and SC-20179 for Sept4 from Santa Cruz Biotechnology (Santa Cruz, Calif.).

Protein production and purification: GST-Parkin was produced as described (Fallon et al., *Nat. Cell Biol* 8(8) 834-842 (2006)). Sept4 protein was produced as a GST fusion protein and cleaved as described (Ihara et al., *Neuron* 53:519-533 (2007)). E1, UbcH7 (E2) and ubiquitin were purchased from Boston Biochem (Cambridge, Mass.).

Cell Transfections, epoxomicin treatment: Fugne6 (Roche, Calif.) was used to introduce 1 ug total of cDNA into HEK293 cells. After 24 hours cells were treated with 100 nM epoxomicin (Boston Biochem) in DMSO or DMSO alone. Sixteen hours after epoxomicin, cells were lysed into IPB buffer as described (Johnston et al, *JCB* 143:1883-1898 (1998)) and equal protein amounts of soluble lysate were loaded on 10% Tris-Glycine SDS-PAGE and immunoblotted.

Co-immunoprecipitation experiments: Cells were washed twice with PBS, harvested and stored at −20 degrees overnight. Thawed HEK cells were lysed with 50 mM Hepes 50 mM NaCl pH7.5, HCC were lysed with IPB buffer, protein content measured (Bradford Assay, BioRad) and 1 ug of 1A1 Parkin antibody was added to pre-cleared lysates for 3-16 hours. Pre-cleared Protein G-Sepharose beads (GE Healthcare) were added for an additional 1 hour with rotation, beads were washed three times with lysis buffer and proteins were eluted from the beads using SDS-PAGE sample buffer for immunoblotting analysis.

In vitro ubiquitinylation assays: 50 ul reactions were assembled under the following conditions: 50 mM Hepes 50 mM NaCl, pH8.8, 5 uM E2, 400 nM E1, 200 uM ubiquitin, 1 uM Sept4, and 3.75 ug GST-Parkin, Siah1, Nedd, E6-AP of MURF1. Assays were assembled on ice and 15 ul aliquots were removed into SDS-PAGE sample buffer after 0, 30 and 60 minutes incubation at 37 degrees. Samples were analyzed via 10% Tris-Glycine SDS-PAGE and immunoblotting.

Example 2

Parkin and Sept4 Interact in Two-Hybrid Screens

Yeast-two hybrid screens were used to identify human proteins that interact with human Parkin. A comparison of the results from a screen using the first 237 amino acids (1-237) of the Parkin protein and the full length Parkin protein (FL) revealed one result overwhelmingly represented: Septin 4 protein (Sept4, NM_080416.1). Various independent isolates spanned the entire region of Sept 4 from amino acid 117 to the C-terminus. Because we identified Sept4 clones from the 1-237 screen, the interaction domain of Parkin for Sept4 is in the amino terminal of Parkin (FIG. 1). We did not find any clones covering the first 117 amino acids of Sept4.

Example 3

Parkin and Sept4 Interact in Co-Immunoprecipitation Experiments

In order to establish that the Sept4 interacts with Parkin co-immunoprecipitation (CO-IP) experiments were performed. As shown in FIG. 1b, Parkin antibodies are able to specifically CO-IP Parkin and Sept4 when Sept4 cDNA is transfected into HEK293 cells stably expressing Parkin (HEK-Parkin). CO-IP from HEK-Parkin cells transfected with a pcDNA vector control did not precipitate Sept4 immunoreactive material. Moreover, using human cortical neurons (HCC) transduced with lentivirus encoding Parkin, Parkin antibodies are able to specifically CO-IP Parkin and endogenous Sept4 (FIG. 2b, HCC+Parkin). There was no immuno-isolation of Sept4 from control cells transduced with the LV-vector alone (FIG. 2b, HCC control).

Example 4

Ubiqutination of Sept4 In Vivo

To determine if the Sept4 can be multiubiquitinylated in cells, 293 HEK cells were transfected with the Sept4 and pcDNA, or Sept4 and Parkin, followed by the addition of proteasome inhibitor. Immunoblots of cellular lysates using Sept4 antibodies demonstrate the addition of proteasome inhibitor has increased the overall amount of Sept4 in the lysates, and has also resulted in the accumulation of high molecular weight species of Sept4 (FIG. 1d). Moreover, in the presence of the Parkin, there is a marked increased level of the higher molecular weight species of Sept4 suggesting that Parkin may play a role in the ubiquitination and turnover of Sept4 by 26S proteasomes.

Example 5

Ubiquitination of Sept4 is Mediated by Parkin In Vitro

Figure 2:
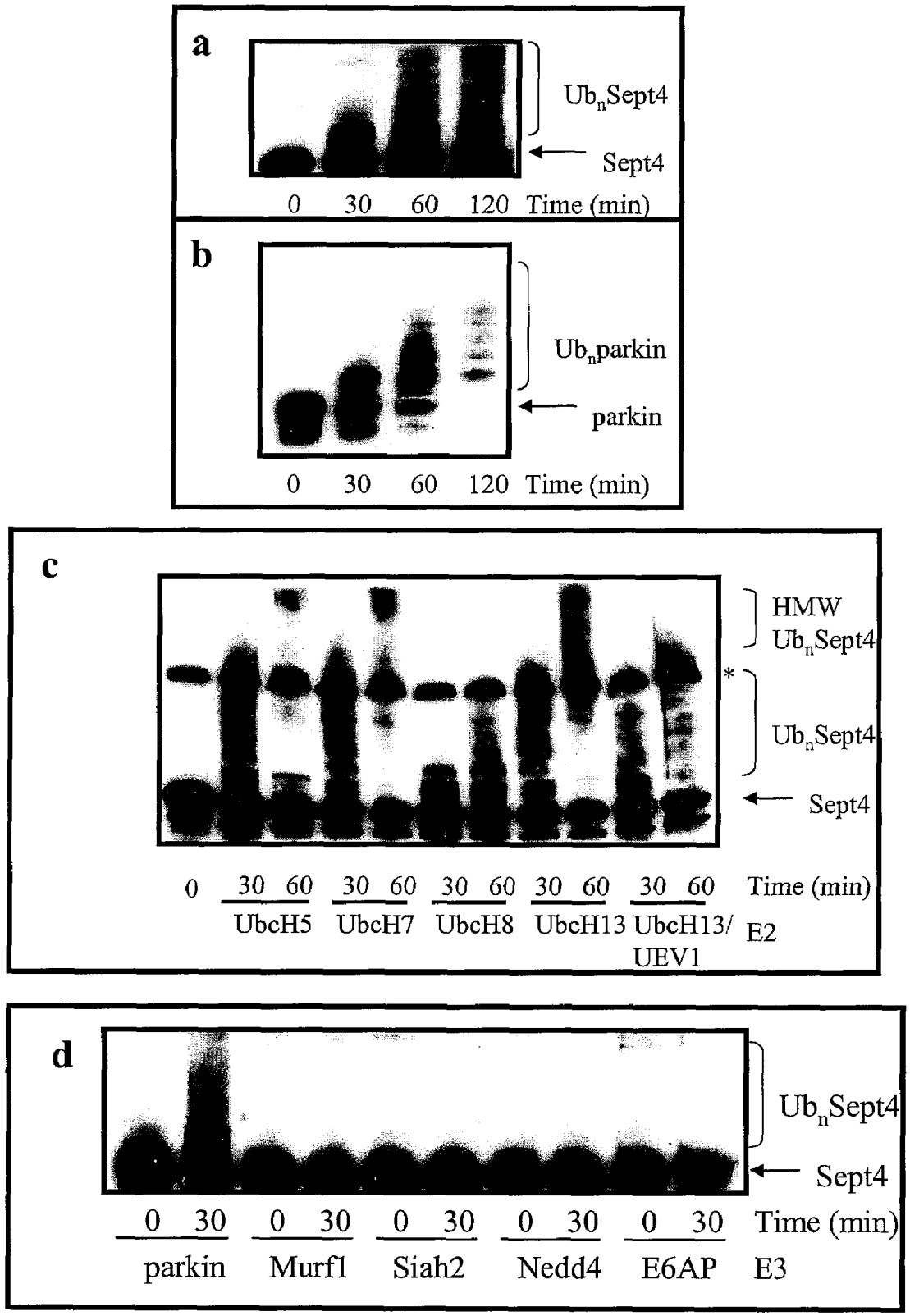
FIG. 2 is a Western blots showing that Parkin mediates the ubiquitinylation of Sept4 in vitro. Purified Sept4 was incubated with GST-E1, UbcH8, Ub, ATP and GST-Parkin at 37° C. for the times indicated. Samples were run on 10% SDS-PAGE and Western blotted.

To directly demonstrate the relationship of Sept4 and Parkin the Sept4 and Parkin proteins were purified. In vitro assays were performed to assess the ubiquitinylation of Sept4 in the presence of enzymatically active Parkin. As demonstrated in FIG. 2, purified Sept 4 is multiubiquitinylated by Parkin. Parkin activity is demonstrated in FIG. 2b, where the aliquots from the same reaction as in FIG. 2a are immunoblotted with antibodies to Parkin, demonstrating robust autoubiquitinylation. These reactions used UbcH8, an E2 enzyme that was reported to be required for Parkin activity for Sept5 protein, and it is clearly active for the Sept4 protein. However, in a survey of various E2 enzymes for Parkin-Sept4 activity, we found that UbcH5, UbcH7, UbcH13, UbcH13/Uev1 can also ubiquitinylate Sept4, and in fact do so to a greater extent than UbcH8 (FIG. 2c). The implications of these results are that Parkin may be a ligase that can function in many different cellular regulatory roles with different E2 enzymes. Sept4 ubiquitinylation is relatively specific to Parkin, as a variety of other ligases were not able to ubiquitinylate Sept4 (FIG. 2d). Because no instance of monoubiquitinate of Sept4 by Parkin was observed (regardless of E2 utilized in the reaction, FIG. 2c), and since the addition of proteasome inhibitors to cells causes an increase in Sept4 levels (FIG. 1d), it is likely that Parkin is targeting Sept4 protein for degradation by the 26S proteasome.

Example 6

Thermal Denaturation Screening Assay Using Septin4 as Substrate

In one aspect of the invention, Septin4 may be used as a Parkin substrate in a thermal denaturation assay as described in U.S. provisional application No. 61/025,231, filed Jan. 31, 2008 and incorporated herein by reference. Briefly, the thermal denaturation assay is an in vitro screening assay to identify candidate compounds for prevention and treatment Parkinson's Disease. Parkin protein ("parkin") is exposed to conditions ("thermal destabilization conditions") that cause loss of parkin ligase activity. The exposure to thermal destabilization conditions is carried out in the presence or absence of test agents. Agents that preserve parkin ligase activity are candidate compounds for treatment of Parkinson's Disease.

In one version the screening assay involves a) exposing a plurality of test samples to thermal destabilization conditions, where each test sample contains i) parkin protein and ii) one of a plurality of test agents; b) determining parkin ligase activity in said test samples relative to a control sample comprising parkin protein exposed in the absence of a test agent to the thermal destabilization conditions, where a test agent contained in a test sample in which parkin ligase activity exceeds the ligase activity in the control sample is identified as a candidate compound for treatment of Parkinson's Disease. In one embodiment the parkin exposed in the absence of a test agent to the thermal destabilization conditions retains 40-70% of the its original E3 ligase activity. Examples of thermal destabilization conditions include incubation at a temperature of from 45° C. to 60° C. for 30 minutes to 180 minutes. For illustration, incubation can be at about 57° C. for about 90 minutes or about 60° C. for about 150 minutes.

In a version of the assay, parkin ligase activity can be determined by combining parkin protein, an E1 ubiquitin-activating enzyme, an E2 ubiquitin-conjugating enzyme, ATP, ubiquitin, and Septin 4 in an appropriate buffer, incubating the combination at 20-37° C. and measuring the rate or extent of ubiquitination of the parkin substrate.

In the assay parkin ligase activity can be determined using a Fluorescence Resonance Energy Transfer (FRET) assay in which a donor chromophore is associated with ubiquitin and an acceptor chromophore is associated with a parkin substrate, or in which a donor chromophore is associated with parkin substrate and an acceptor chromophore is associated with a ubiquitin. In an embodiment the donor chromophore is europium cryplate and the acceptor chromophore is allophycocyanin.

Positive modulators of parkin activity that are parkin stabilizers may be distinguished from candidate compounds that are parkin agonists by incubating unattenuated parkin protein in the presence and absence of said compound, where a compound that increases parkin ligase activity is identified as a parkin agonist and a compound that does not increase parkin ligase activity is identified as a parkin stabilizer.

* * *

All publications and patent documents (patents, published patent applications, and unpublished patent applications) cited herein are incorporated herein by reference as if each such publication or document was specifically and individually indicated to be incorporated herein by reference. Citation of publications and patent documents is not intended as an admission that any such document is pertinent prior art, nor does it constitute any admission as to the contents or date of the same. The invention having now been described by way of written description and example, those of skill in the art will recognize that the invention can be practiced in a variety of embodiments and that the foregoing description and examples are for purposes of illustration and not limitation of the following claims.

What is claimed is:

1. A cell-based method for measuring Parkin activity comprising:
   (a) providing a mammalian cell expressing Parkin and expressing Sept4, wherein the Parkin is expressed recombinantly in the cell; and
   (b) measuring the rate or extent of Sept4 ubiquitination in the cell, whereby Parkin activity is measured.

2. The method of claim 1 in which the Sept4 protein is expressed endogenously in the cell.

3. The method of claim 1 in which the Sept4 protein is expressed recombinantly in the cell.

4. The method of claim 1 wherein the Parkin protein is a variant or fragment of wild-type human Parkin.

5. The method of claim 4 in which the Parkin protein is a variant having asparagine instead of serine at position 167; tyrosine instead of cysteine at position 212;
   methionine instead of threonine at position 240; tryptophan instead of arginine at position 275;

glycine instead of cysteine at position 289; or leucine instead of proline at position 437.

6. An ex vivo cell-based assay for modulators of Parkin activity, said assay comprising:
  (a) providing a mammalian cell expressing Parkin and expressing Sept4, wherein the Parkin is expressed recombinantly in the cell;
  (b) exposing the cell to a test agent; and
  (c) comparing the rate or extent of Sept4 ubiquitination in the cell in the presence of the test agent with the rate or extent of Sept4 ubiquitination in a control cell not exposed to the test agent, where a relative increase in Sept4 ubiquitination in the presence of the test agent indicates that the test agent enhances Parkin ubiquitination activity and a relative decrease in Sept4 ubiquitination in the presence of the test agent indicates that the test agent inhibits Parkin ubiquitination activity.

7. The assay of claim 6 in which the Sept4 protein is expressed endogenously in the cell.

8. The assay of claim 6 in which the Sept4 protein is expressed recombinantly in the cell.

9. The assay of claim 6 wherein the Parkin protein is a variant or fragment of wild-type human Parkin.

10. The assay of claim 9 in which the Parkin protein is a variant having asparagine instead of serine at position 167; tyrosine instead of cysteine at position 212; methionine instead of threonine at position 240; tryptophan instead of arginine at position 275; glycine instead of cysteine at position 289; or leucine instead of proline at position 437.

* * * * *